| United States Patent [19] | [11] 4,049,422 |
|---|---|
| Shen et al. | [45] Sept. 20, 1977 |

[54] HERBICIDAL MORPHOLINOBENZIMIDAZOLES

[75] Inventors: Kelvin Kei-Wei Shen, Fountain Valley; Wayne Stuart Belles, Orange, both of Calif.

[73] Assignee: United States Borax & Chemical Corporation, Los Angeles, Calif.

[21] Appl. No.: 671,452

[22] Filed: Mar. 29, 1976

[51] Int. Cl.² ............... A01N 9/22; C07D 498/04
[52] U.S. Cl. ............................... 71/92; 544/101
[58] Field of Search ............... 71/92; 260/247.5 EP

[56] References Cited
PUBLICATIONS

Nair et al., J. Am. Chem. Soc., vol. 83, pp. 3518–3521, (1961).

*Primary Examiner*—Lewis Gotts
*Assistant Examiner*—Catherine L. Mills
*Attorney, Agent, or Firm*—James R. Thornton

[57] ABSTRACT

Tricyclic 1,2-morpholinobenzimidazoles having a haloalkyl, alkylsulfonyl, haloalkylsulfonyl, halo or lower alkyl substituent on the aromatic ring para to the morpholino nitrogen. The aromatic ring and morpholino ring may also have other substituents. The compounds are herbicidal, useful as pre-emergence or post-emergence treatments.

18 Claims, No Drawings

HERBICIDAL MORPHOLINOBENZIMIDAZOLES

This invention relates to herbicidal compounds useful in controlling weeds, and it relates especially to a class of herbicidal tricyclic morpholinobenzimidazole compounds which may also be named as 1,2-(gamma-oxa-tetramethylene)benzimidazoles.

BACKGROUND OF THE INVENTION

The synthesis of certain morpholinobenzimidazole compounds is described by Nair and Adams in the *Journal of the American Chemical Society*, Volume 83, pages 3518–3521 (1961). These compounds are prepared by the oxidative cyclization of the corresponding ortho-anilinomorpholine compound with peroxytrifluoroacetic acid according to the following reaction

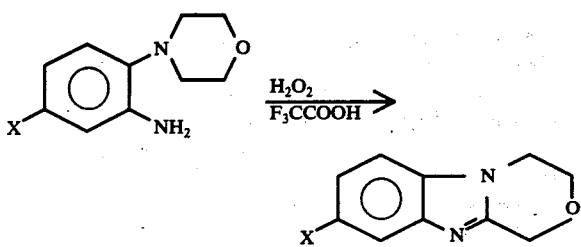

in which X equals hydrogen, chloro, methyl or nitro. The peroxytrifluoroacetic acid is prepared in situ by using trifluoroacetic acid (or anhydride) and 30% hydrogen peroxide. Solvents such as methylene chloride are generally suitable for the reaction. The ortho-anilinomorpholines can be prepared by catalytic or chemical reduction of the corresponding ortho-nitrophenylmorpholine compounds.

SUMMARY OF THE INVENTION

It has been found that a class of 1,2-morpholinobenzimidazole compounds of the following formula

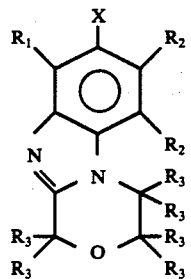

are useful as herbicides, in which X represents halo-lower alkyl, lower alkylsulfonyl, halo-lower alkylsulfonyl, halo or lower alkyl, $R_1$ represents hydrogen, lower alkyl or halo, each $R_2$ is selected from hydrogen, halo, lower alkyl, lower alkoxy, cyano, amino and nitro and each $R_3$ is selected from hydrogen and lower alkyl. The term "lower alkyl" and "lower alkoxy" when used herein is meant to include alkyl and alkoxy groups having up to about six carbon atoms, either straight or branched chain. Examples of groups which may be represented by X, $R_1$, $R_2$ and/or $R_3$ include methyl, ethyl, isopropyl, tertiary-butyl, secondary-pentyl, n-hexyl, sec-butyl, methoxy, ethoxy, n-butoxy, trifluoromethyl, dichloromethyl, pentafluoroethyl, beta-bromoethyl, heptafluoro-n-propyl, methyl-sulfonyl chloromethyl, ethylsulfonyl, n-propylsulfonyl, trifluoromethylsulfonyl, difluoromethylsulfonyl, dichloromethylsulfonyl, chloro, bromo, fluoro, and the like.

A preferred group of novel compounds is also provided by this invention. This class of compounds possesses a high level of herbicidal activity at low rates of application. Such compounds may be defined by the above formula in which X represents trifluoromethyl, lower alkylsulfonyl, halo-lower alkylsulfonyl, or branched-chain alkyl of three to about six carbon atoms, $R_1$ represents hydrogen, chloro or $C_1$–$C_3$ alkyl, each $R_2$ represents hydrogen, chloro, $C_1$–$C_3$ alkyl, amino or nitro, and each $R_3$ represents hydrogen or $C_1$–$C_3$ alkyl. Such compounds are superior herbicides, especially when applied as pre-emergence treatments and incorporated in the upper layer of the soil prior to planting the crop.

Although the compounds may be generically described as 1,2-morpholinobenzimidazoles, in order to name specific compounds, a more definite designation of substituent locations on the basic tricyclic molecule is necessary. Thus, $R_1$ represents the substituent at the 4-position of the aromatic ring. X represents the 5-substituent. The $R_2$ located adjacent to X represents the 6-position, and the second $R_2$ group represents the 7-position. On the morpholino ring, the various positions are represented by the Greek letters. Therefore, the carbon adjacent to the ring-nitrogen is defined as the alpha position, with the next carbon--going clockwise around the ring--being the beta-position. The oxygen is at the gamma-position and the next carbon atom is at the delta-position. Therefore, the groups represented by $R_3$ may be at the alpha, beta or delta positions of the morpholino ring. The basic molecule can thus be named 1,2-(gamma-oxa-tetramethylene)benzimidazole. Alternatively, the compounds can be named as 3,4-dihydro-1H-[1,4]-oxazino-[4,3-a]benzimidazoles in which X in the above formula represents the substituent at the 8-position.

Compounds of this invention may be prepared according to the procedure of Nair and Adams. An alternative consists of a two-step reaction involving formation of the N-oxide by cyclization of the corresponding ortho-nitrophenylmorpholine compound by use of refluxing hydrochloric acid. The benzimidazole-N-oxide is then reduced, such as with hydrogen over platinum catalyst, to give the desired 1,2-morpholinobenzimidazole. The synthesis can be illustrated by the following equation.

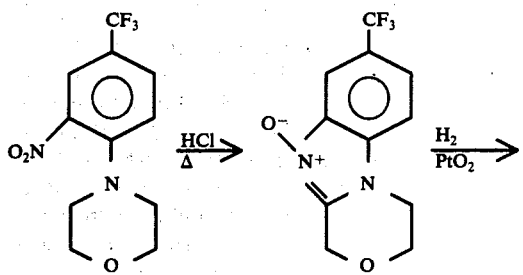

-continued

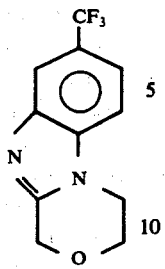

In some cases, it is desirable to add the aromatic ring substituents after formation of the morpholinobenzimidazole, such as by nitration, halogenation, etc. according to known procedures.

The following examples illustrate preparation of representative compounds of this invention.

EXAMPLE 1

4-(2-Nitro-4-trifluoromethylphenyl)morpholine

4(2-Nitro-4-trifluoromethylphenyl)morpholine was prepared by reaction of 4-chloro-3-nitrobenzotrifluoride with equimolar amounts of morpholine and triethylamine in monoglyme. The resultant product melts at 37° – 39° C.

EXAMPLE 2

4(2Amino-4-trifluoromethylphenyl)morpholine 4-(2Nitro-4-trifluoromethylphenyl)morpholine was hydrogenated over palladium on carbon catalyst in monoglyme to give the corresponding 2-amino compound which melts at 126°–129° C.

EXAMPLE 3

5-Trifluoromethyl-1,2-(gamma-oxa-tetramethylene)-benzimidazole

To a stirred solution of 3.0 grams of 4-(2-amino-4-trifluoromethylphenyl)morpholine dissolved in 18 ml. of 88% formica acid was added, dropwise, 6ml. of 30% hydrogen peroxide. The resultant solution was heated gradually to about 60° C., at which temperature an exothermic reaction took place, and then heated at 75° C. for 15 minutes. An equal volume of ice water was added to the mixture, and the supernatant was decanted. The aqueous solution was neutralized with ammonium hydroxide and then extracted twice with methylene chloride. The combined extracts were dried and the solvent evaporated under reduced pressure. The crystalline residue was recrystallized from a chloroform-n-hexane mixture to give a 46% yield of product melting at 130°–132° C.

EXAMPLE 4

5-Trifluoromethyl-6-nitro-1,2-(gamma-oxa-tetramethylene)benzimidazole

5-Trifluoromethyl-1,2-(gamma-oxa-tetramethylene) benzimidazole (2.0 grams) was dissolved in 15 ml. of sulfuric acid. This solution was cooled in an ice water bath and 90% nitric acid (1.74 grams) was added dropwise. The mixture was stirred at room temperature for two hours and then poured into ice water. Neutralization with 10% sodium hydroxide precipitated the product, which was isolated by filtration and dried to give 2.2 grams (92% yield) which melted at 186°–187° C.

EXAMPLE 5

6-Amino-5trifluoromethyl-1,2-(gamma-oxa-tetramethylene)benzimidazole

5-Trifluoromethyl-6-nitro-1,2-(gamma-oxa-tetramethylene)benzimidazole (1.77 grams) dissolved in 60 ml. of methanol and 60 ml. of monoglyme was hydrogenated in the presence of 0.1 g. of palladium on carbon (10%) catalyst. The resultant solution was filtered and the solvent removed by evaporation under reduced pressure to give a crystalline residue which was recrystallized from chloroform, giving 1.55 grams (97.3% yield) of the desired product melting at 204°–205° C.

EXAMPLE 6

5-Trifluoromethyl-6-amino-7-chloro-1,2-(gamma-oxa-tetramethylene)benzimidazole

6-Amino-5-trifluoromethyl-1,2-(gamma-oxa-tetramethylene)benzimidazole (0.95 grams) was dissolved in 15 ml. of glacial acetic acid. To this solution was added, dropwise, 0.55 gram of sulfuryl chloride at about 13° C. The mixture was stirred at ambient temperature for about 15 minutes and then poured into water. The pH of the aqueous solution was adjusted to about 6 and the precipitated product removed by filtration and washed with water to give 0.9 gram of product melting at 156°–157° C.

EXAMPLE 7

5-Trifluoro-6-chloro-7-nitro-1,2-(gamma-oxa-tetramethylene)benzimidazole

To a cooled and stirred mixture of 3.5 grams of 90% nitric acid and 5.4 grams of 30% oleum plus 2 ml. of 98% sulfuric acid was added 5.0 grams of 6-chloro-5-trifluoromethyl-1,2-(gamma oxa-tetramethylene)benzimidazole. The resultant mixture was stirred at room temperature overnight and then poured into 100 grams of ice. The pH was adjusted with 10% sodium hydroxide to 8 and the resultant mixture extracted twice with chloroform. The combined extracts were dried over sodium sulfate and a portion of the solvent was removed by distillation under reduced pressure. To the hot residue was added n-hexane. Upon cooling, the product melting at 196°–197.5° C. (5.5 grams; 95% yield) was obtained.

EXAMPLE 8

5-Trifluoromethyl-6-chloro-7-amino-1,2-(gamma-oxa-tetramethylene)benzimidazole

5-Trifluoromethyl-6-chloro-7-nitro-1,2-(gamma-oxa-tetramethylene)benzimidazole dissolved in dimethoxyethane-methanol was hydrogenated over platinum oxide catalyst to give the corresponding 7-amino compound, melting at 212°–212.5° C. (92% yield).

EXAMPLE 9

4,6,7-Trichloro-5-trifluoromethyl-1,2-(gamma-oxa-tetramethylene)benzimidazole

To a stirred and cooled solution of 40 ml. of sulfuryl chloride was added 5.0 grams of 4-(2-amino-4-trifluoromethylphenyl)morpholine. The resultant mixture was allowed to warm to room temperature and evaporated to dryness under reduced pressure. Cold water (40 ml.) was added to the residue and the solution adjusted to pH 8 with aqueous sodium hydroxide. The aqueous solution was extracted twice with 60 ml. of chloroform.

The combined chloroform extracts were dried and evaporated to dryness under reduced pressure to give 1.8 grams (30%) of the desired product, melting at 156°–158° C.

EXAMPLE 10

5-Trifluoromethyl-1,2-(gamma-oxa-tetramethylene)-benzimidazole

5-Trifluoromethyl-1,2-(gamma-oxa-tetramethylene)-benzimidazole-N-oxide (1.1 gram) was hydrogenated in methanol over 0.5 gram of platinum oxide (85%) catalyst. Evaporation of the solvent gave a residue which was extracted with chloroform. The chloroform soluble material was found to be the desired product (0.97 gram; 88% yield), melting at 129°–131° C.

The following are examples of additional compounds coming within the scope of this invention which may be prepared according to the procedure described above.

6-chloro-5-trifluoromethyl-1,2-(gamma-oxa-tetramethylene)benzimidazole, m.p. 160°–161° C.
5-methyl-1,2-(gamma-oxa-tetramethylene)benzimidazole, m.p. 165°–168° C.
5-chloro-1,2-(gamma-oxa-tetramethylene)benzimidazole, m.p. 180°–185° C.
5-trifluoromethyl-1,2-(beta, delta-dimethyl-gamma-oxa-tetramethylene)benzimidazole; oil
7-nitro-5-trifluoromethyl-1,2-(gamma-oxa-tetramethylene)benzimidazole, m.p. 204°–205° C.
7-amino-5-trifluoromethyl-1,2-(gamma-oxa-tetramethylene)benzimidazole, m.p. 150°–152° C.
5-methylsulfonyl-1,2-(gamma-oxa-tetramethylene)benzimidazole, m.p. 214°–215° C.
5-tert.butyl-1,2-(gamma-oxa-tetramethylene)benzimidazole, m.p. 127°–130° C.
5-trifluoromethyl-7-chloro-1,2-(gamma-oxa-tetramethylene)benzimidazole, m.p. 110°–112° C.
5-fluoro-1,2-(gamma-oxa-tetramethylene)benzimidazole, m.p. 126°–128° C.
5-isopropyl-1,2-(gamma-oxa-tetramethylene)benzimidazole, m.p. 95°–97.5° C.
5-trifluoromethyl-1,2-(gamma-oxa-delta-methyl-tetramethylene)benzimidazole, m.p. 114°–116° C.
5-trifluoromethyl-1,2-(beta-methyl-gamma-oxa-tetramethylene) benzimidazole, m.p. 155°–156° C.
5-trifluoromethyl-1,2-(alpha-ethyl-gamma-oxa-tetramethylene)benzimidazole, m.p. 108°–109° C.
5-isopropyl-1,2-(gamma-oxa-delta-methyl-tetramethylene)benzimidazole, m.p. 91°–93° C.
5-isopropyl-1,2-(beta-methyl-gamma-oxa-tetramethylene)benzimidazole, m.p. 148°–150° C.
5-trifluoromethyl-1,2-(alpha, alpha-dimethyl-gamma-oxa-tetramethylene)benzimidazole, m.p. 82°–84° C.
5-trifluoromethyl-1,2-(cis-beta, delta-dimethyl-gamma-oxa-tetamethylene)benzimidazole, m.p. 83°–85° C.
5,6-dichloro-1,2-(gamma-oxa-tetramethylene)benzimidazole, m.p. 187°–189.5° C.
5-methyl-6-chloro-1,2-(gamma-oxa-tetramethylene)-benzimidazole, m.p. 191°–193° C.
5,6-dimethyl-1,2(gamma-oxa-tetramethylene)benzimidazole, m.p. 187.5°–188.5° C.
5-trifluoromethyl-1,2-(trans-beta, delta-dimethyl-gamma-oxa-tetramethylene)benzimidazole, m.p. 95°–98° C.
5-difluoromethylsulfonyl-1,2-(gamma-oxa-tetramethylene)benzimidazole, m.p. 173°–174° C.
5-trifluoromethyl-1,2-(gamma-oxa-delta-ethyl-tetramethylene)benzimidazole, m.p. 133°–134° C.
5-trifluoromethyl-1,2-(beta-ethyl-gamma-oxa-tetramethylene)benzimidazole, m.p. 122°–123° C.
5-trifluoromethyl-6-methoxy-1,2-(gamma-oxa-tetramethylene)benzimidazole, m.p. 118°–120° C.
5-trifluoromethyl-6-cyano-1,2-(gamma-oxa-tetramethylene)benzimidazole, m.p. 188°–190° C.
5-methylsulfonyl-6-methoxy-1,2-(gamma-oxa-tetramethylene)benzimidazole, m.p. 209°–212° C.
5-chloro-6-methyl-7-amino-1,2-(gamma-oxa-tetramethylene)benzimidazole, m.p. 260°–262° C.
5-chloro-6-methyl-7-nitro-1,2-(gamma-oxa-tetramethylene)benzimidazole, m.p. 244.5°–246° C.
5-methylsulfonyl-6-chloro-1,2-(gamma-oxa-tetramethylene)benzimidazole, m.p. 219°–221° C.
5-methylsulfonyl-6-ethoxy-1,2-(gamma-oxa-tetramethylene)benzimidazole
5-bromo-1,2-(gamma-oxa-tetramethylene)benzimidazole
5-ethylsulfonyl-6-chloro-1,2-(gamma-oxa-tetramethylene)benzimidazole
4-chloro-5-dichloromethyl-1,2-(gamma-oxa-tetramethylene)benzimidazole
5-trichloromethyl-1,2-(gamma-oxa-tetramethylene)benzimidazole
5-sec-pentyl-7-chloro-1,2-(gamma-oxa-tetramethylene)-benzimidazole
5-trifluoromethyl-6-bromo-7-amino-1,2-(gamma-oxa-tetramethylene)benzimidazole
5-pentafluoroethyl-1,2-(gamma-oxa-tetramethylene)-benzimidazole The compounds of this invention are excellent herbicides and can be applied as either a pre-emergence or a post-emergence treatment; that is, they can be applied to soil in which the weeds will grow to kill or suppress the emergence of seedlings of undesirable plants or they can be applied to the foliage of the growing plants after emergence from the soil. Thus, the compounds can be used to control the growth of weeds by applying a phytotoxic amount of one or more of the active compounds of this invention to the locus to be protected; that is, soil in which the weeds are growing or will grow or the foliage of the growing plants. When used as a pre-emergence treatment, it is preferred that the compounds be incorporated, such as by mixing into the top 1 to 3 inches of the soil, prior to planting the crop. When used as a post-emergence treatment, it is preferred that a directed spray be employed, thereby directing the application of the herbicide unto the foliage of the weeds and away from the foliage of the crop plants. Weeds, as used herein, is meant to include any plant growth which is undesirable.

The compounds are especially useful for selectively controlling weeds in the presence of desirable crops such as peanuts, corn, soybeans, rice, and in some cases, cotton. The weeds controlled include many of the broadleaf and grassy weeds such as lambsquarter, mustard, pigweed, sesbania, velvetleaf, morningglory, cocklebur, johnsongrass, wild oats, barnyard grass, etc.

Generally, an application rate of from about 0.2 to about 15 pounds of one or more of the active compounds per acre is effective in controlling weed growth. Preferably, when used as a pre-emergence treatment, an application rate in the range of about 0.5 to 5 pounds per acre is employed. Lower amounts can be employed when the compound is incorporated, which is the preferred pre-emergence treatment. When used as a post-emergence treatment, it is preferred that an application rate in the range of about 0.5 to 4 pounds per acre be used.

The following examples illustrate the herbicidal activity of representative compounds of this invention.

EXAMPLE 11

The compounds to be tested were evaluated as both a pre-emergence and post-emergence treatment. Greenhouse flats were planted to soybeans (SB), velvetleaf (VL), oats (O) and millet (M). The flats were sprayed on the same day as planting with an ethanol solution (sometimes containing added dioxane) of the compound to be tested at a rate of 5 pounds per acre. Another set of flats with the same plants was treated after the plants had emerged and were about one inch in height. These flats were also sprayed with the solution of the compound to be tested at a rate of 5 pounds per acre. The flats were kept in the greenhouse and watered when needed. Twenty-one days after treatment, the flats were examined and the plants rated for herbicidal activity on a 0 – 9 scale in which 0 = no effect, 5 = substantial injury with some kill and 9 = complete kill. Results are shown in Table I.

The compounds in the table are all based on the parent 1,2-(gamma-oxa-tetramethylene)benzimidazole molecule (OTB) having the indicated substituents designated as follows.

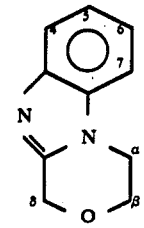

TABLE I

| | Activity | | | | | | | |
| | Pre | | | | Post | | | |
| Compound | SB | VL | O | M | SB | VL | O | M |
|---|---|---|---|---|---|---|---|---|
| 5-Trifluoromethyl-OTB | 9 | 9 | 9 | 9 | 9 | 9 | 9 | 9 |
| 4,6,7-trichloro-5-trifluoromethyl-OTB | 0 | 0 | 0 | 1 | 1 | 6 | 0 | 0 |
| 5-trifluoromethyl-6-chloro-OTB | 3 | 9 | 4 | 9 | 9 | 9 | 9 | 9 |
| 5-trifluoromethyl-6-chloro-7-nitro-OTB | 1 | 9 | 1 | 6 | 1 | 9 | 1 | 8 |
| 5-trifluoromethyl-6-chloro-7-amimo-OTB | 1 | 9 | 7 | 9 | 6 | 9 | 5 | 9 |
| 5-methyl-OTB | 3 | 9 | 8 | 9 | 6 | 9 | 5 | 9 |
| 5-chloro-OTB | 3 | 9 | 5 | 9 | 6 | 9 | 5 | 9 |
| 5-isopropyl-OTB | 9 | 9 | 9 | 9 | 9 | 9 | 9 | 9 |
| 5-tert.-butyl-OTB | 4 | 9 | 8 | 9 | 9 | 9 | 9 | 9 |
| 5-trifluoromethyl-7-chloro-OTB | 3 | 9 | 6 | 9 | 8 | 9 | 8 | 9 |
| 5-methylsulfonyl-OTB | 6 | 9 | 9 | 8 | 9 | 9 | 9 | 9 |
| 5-trifluoromethyl-beta,delta-dimethyl-OTB | 4 | 9 | 5 | 6 | 5 | 9 | 5 | 9 |
| 5-trifluoromethyl-7-nitro-OTB | 0 | 8 | 2 | 7 | 1 | 9 | 0 | 0 |
| 5-trifluoromethyl-7-amino-OTB | 0 | 1 | 0 | 5 | 1 | 9 | 0 | 8 |
| 5-trifluoromethyl-6-amino-OTB | 0 | 7 | 1 | 0 | 2 | 9 | 0 | 8 |
| 5-trifluoromethyl-6-amio-7-chloro-OTB | 4 | 9 | 8 | 9 | 7 | 9 | 7 | 9 |
| 5-fluoro-OTB | 0 | 9 | 2 | 2 | 1 | 9 | 1 | 0 |
| 5-trifluoromethyl-delta-methyl-OTB | 4 | 9 | 9 | 9 | 9 | 9 | 9 | 9 |
| 5-trifluoromethyl-beta-methyl-OTB | 1 | 6 | 2 | 2 | 4 | 9 | 2 | 8 |
| 5-trifluoromethyl-alpha-ethyl-OTB | 0 | 0 | 0 | 0 | 3 | 8 | 1 | 6 |
| 5-trifluoromethyl-alpha,alpha-dimethyl-OTB | 1 | 0 | 1 | 0 | 2 | 9 | 1 | 8 |
| 5-isopropyl-delta-methyl-OTB | 3 | 9 | 7 | 8 | 9 | 9 | 5 | 9 |
| 5,6-dichloro-OTB | 0 | 0 | 0 | 0 | 2 | 7 | 0 | 0 |
| 5-methyl-6-chloro-OTB | 0 | 0 | 0 | 0 | 1 | 7 | 1 | 0 |
| 5,6-dimethyl-OTB | 0 | 0 | 0 | 0 | 2 | 9 | 1 | 6 |
| 5-isopropyl-beta-methyl-OTB | 0 | 9 | 0 | 2 | 4 | 9 | 2 | 8 |
| 5-trifluoromethyl-6-methoxy-OTB | 1 | 0 | 0 | 0 | 1 | 7 | 1 | 7 |
| 5-trifluoromethyl-6-cyano-OB | 0 | 0 | 0 | 0 | 1 | 6 | 1 | 0 |

EXAMPLE 12

Several compounds were evaluated as post-emergence herbicides in greenhouse tests with a broad group of crops and weeds. The compounds were applied at 1 and 2 pounds per acre to the plants when they were about one inch in height. Twenty-one days after treatment, the plants were rated on a 0 to 9 scale. Where two numbers are used, i.e. 8/4, the first number represents the percent kill and the second number is the injury to the remaining plants, using the following scale.

0 = no effect
1 = < 10% injury
2 = 10–40% injury
3 = 40–70% injury
4 = > 70% injury
5 = < 25% kill
6 = 25–50% kill
7 = 50–75% kill
8 = 75–99% kill
9 = 100% kill The results are given in Table II and are an average of two replicates, in which:

Compound A = 5-trifluoromethyl-6-chloro-1,2-(gamma-oxa-tetramethylene)benzimidazole
Compound B = 5-trifluoromethyl-1,2-(gamma-oxa-tetramethylene)benzimidazole
Compound C = 5-trifluoromethyl-7-amino-1,2-(gamma-oxa-tetramethylene)benzimidazole

TABLE II

| Plant | Compound A 1 lb. | Compound A 2 lb. | Compound B 1 lb. | Compound B 2 lb. | Compound C 1 lb. | Compound C 2 lb. |
|---|---|---|---|---|---|---|
| lambsquarter | 9 | 9 | 2 | 5/4 | 6/1 | 9 |
| mustard | — | — | 9 | 9 | 7/0 | 8/4 |
| pigweed | 6/2 | 8/3 | 2 | 5/2 | 5/2 | 8/2 |
| sesbania | 9 | 8/4 | 9 | 9 | 7/1 | 9 |
| velvetleaf | 9 | 9 | 9 | 9 | 9 | 9 |
| prickly sida | 2 | 2 | 5/2 | 9 | 8/2 | 8/4 |
| jimsonweed | 9 | 9 | 9 | 9 | 8/2 | 8/4 |
| morningglory | 8/3 | 9 | 6/2 | 9 | 9 | 9 |
| cocklebur | 9 | 9 | 9 | 9 | 9 | 9 |
| johnsongrass | 0 | 6/3 | 5/2 | 7/4 | 0 | 5/1 |
| foxtail | 1 | 3 | 0 | 1 | 0 | 5/1 |
| wild oats | 6/2 | 9 | 5/3 | 8/4 | 0 | 5/1 |
| barnyard grass | 6/3 | 7/4 | 9 | 9 | 0 | 0 |
| alfalfa | 2 | 5/2 | 8/2 | 9 | 5/2 | 8/2 |
| field beans | 3 | 5/1 | 9 | 9 | 6/2 | 6/2 |
| peanuts | 0 | 0 | 0 | 2 | 0 | 2 |
| cotton | 5/2 | 8/1 | 6/4 | 9 | 7/2 | 9 |
| soybeans | 3 | 8/1 | 2 | 8/2 | 2 | 2 |
| wheat | 5/3 | 8/4 | 9 | 9 | 5/1 | 6/1 |
| corn | 0 | 3 | 2 | 3 | 0 | 1 |
| rice | 1 | 2 | 6/4 | 9 | 0 | 1 |

EXAMPLE 13

Several compounds of this invention were also evaluated as pre-emergence herbicides against the same broad group of crops and weeds at 1 and 2 pounds per acre. The greenhouse flats were planted and then on the same day sprayed with an ethanol solution of the compound to be tested. Evaluations were made twenty-one days after treatment as described in Example 12. The results are given in Table III, in which, Compound B = 5-trifluoromethyl-1,2-(gamma-oxa-tetramethylene)benzimidazole
Compound D = 5-trifluoromethyl-6-chloro-7-nitro-1,2-(gamma-oxa-tetramethylene)benzimidazole

TABLE III

| Plant | Compound B 1 lb. | Compound B 2 lb. | Compound D 1 lb. | Compound D 2 lb. |
|---|---|---|---|---|
| lambsquarters | 9 | 9 | 8/4 | 8/3 |
| mustard | 9 | 9 | 8/3 | 8/3 |
| pigweed | 9 | 9 | 0 | 8/3 |
| sesbania | 8/4 | 9 | 2 | 5/3 |
| velvetleaf | 9 | 9 | 0 | 0 |
| prickly sida | 9 | 9 | 0 | 1 |
| jimsonweed | 8/4 | 8/4 | 6/2 | 5/2 |
| morningglory | 8/3 | 7/3 | 0 | 0 |
| cocklebur | 9 | 9 | 0 | 0 |
| johnsongrass | 8/4 | 9 | 0 | 0 |
| foxtail | 8/4 | 8/4 | 0 | 0 |
| wild oats | 8/4 | 8/4 | 0 | 0 |
| barnyard grass | 8/4 | 8/4 | 0 | 0 |
| alfalfa | 8/3 | 9 | 0 | 0 |
| field beans | 9 | 9 | 0 | 0 |
| peanuts | 1 | 2 | 0 | 0 |
| cotton | 9 | 9 | 0 | 0 |
| soybeans | 5/3 | 7/4 | 0 | 0 |
| wheat | 9 | 9 | 0 | 0 |
| corn | 6/3 | 6/3 | 0 | 0 |
| rice | 8/4 | 9 | 0 | 0 |

EXAMPLE 14

Pre-emergence treatments with soil incorporation were also tested. The procedure of Example 13 was repeated except the chemical was incorporated by mixing it into the top one inch prior to planting the seeds.

The results are given in Table IV and are an average of two replicates, in which Compound B = 5-trifluoromethyl-1,2-(gamma-oxa-tetramethylene)benzimidazole
Compound E = 5-methyl-1,2-(gamma-oxa-tetramethylene)benzimidazole
Compound F = 5-isopropyl-1,2-(gamma-oxa-tetramethylene)benzimidazole
Compound G = 5-tert-butyl-1,2-(gamma-oxa-tetramethylene)benzimidazole
Compound H = 5-chloro-1,2-(gamma-oxa-tetramethylene)benzimidazole
Compound J = 5-methylsulfonyl-1,2-(gamma-oxa-tetramethylene)benzimidazole

TABLE IV

| Plants | Compound B 1 lb. | Compound B 2 lb. | Compound E 1 lb. | Compound E 2 lb. | Compound F 1 lb. | Compound F 2 lb. |
|---|---|---|---|---|---|---|
| lambsquarters | 8/3 | 9 | 0 | 2 | 8/4 | 8/4 |
| mustard | 8/4 | 9 | 0 | 5/2 | 8/4 | 8/4 |
| pigweed | 8/3 | 8/4 | 0 | 5/0 | 8/3 | 9 |
| sesbania | 3 | 9 | 9 (?) | 3 | 9 | 9 |
| velvetleaf | 8/4 | 9 | 5/1 | 8/3 | 9 | 9 |
| prickly sida | 7/3 | 7/4 | 2 | 5/2 | 5/2 | 8/4 |
| jimsonweed | 7/3 | 7/4 | 0 | 2 | 7/3 | 8/4 |
| morningglory | 7/3 | 9 | 0 | 2 | 6/3 | 9 |
| cocklebur | 9 | 9 | 5/1 | 2 | 9 | 9 |
| johnsongrass | 7/3 | 8/4 | 2 | 2 | 6/3 | 6/3 |
| foxtail | 2 | 6/3 | 0 | 2 | 6/3 | 8/4 |
| wild oats | 8/4 | 8/4 | 1 | 5/2 | 8/4 | 8/4 |
| barnyard grass | 6/3 | 7/3 | 1 | 2 | 8/4 | 8/4 |
| alfalfa | 5/3 | 8/4 | 0 | 6/2 | 8/4 | 8/4 |
| field beans | 8/4 | 9 | 1 | 6/3 | 8/4 | 9 |
| cotton | 6/3 | 9 | 0 | 1 | 3 | 8/3 |
| soybeans | 4 | 5/4 | 0 | 1 | 4 | 6/4 |
| wheat | 8/4 | 9 | 1 | 3 | 7/4 | 8/4 |
| corn | 3 | 5/3 | 1 | 1 | 2 | 8/2 |
| rice | 5/3 | 7/3 | 0 | 1 | 2 | 3 |
| lambsquarters | 7/3 | 6/3 | 5/2 | 7/3 | 3 | 8/4 |
| mustard | 8/4 | 8/4 | 2 | 3 | 8/4 | 8/4 |
| pigweed | 6/2 | 7/3 | 5/2 | 6/3 | 7/2 | 8/4 |
| sesbania | 0 | 1 | 0 | 0 | 9 | 9 |
| velvetleaf | 9 | 9 | 1 | 7/3 | 8/4 | 9 |
| prickly sida | 7/4 | 8/4 | 0 | 5/3 | 2 | 7/4 |
| jimsonweed | 6/2 | 8/4 | 2 | 7/4 | 7/2 | 7/3 |
| morningglory | 2 | 3 | 0 | 9 | 5/2 | 8/1 |
| cocklebur | 9 | 9 | 0 | 0 | 5/4 | 9 |
| johnsongrass | 8/4 | 8/4 | 1 | 2 | 2 | 6/3 |
| foxtail | 3 | 7/3 | 0 | 1 | 2 | 6/3 |
| wild oats | 8/4 | 8/4 | 1 | 5/3 | 3 | 9 |
| barnyard grass | 6/3 | 8/4 | 1 | 2 | 1 | 5/2 |
| alfalfa | 7/3 | 9 | 2 | 5/2 | 5/1 | 6/2 |
| field beans | 9 | 9 | 0 | 1 | 7/4 | 9 |
| cotton | 1 | 2 | 0 | 1 | 5/4 | 9 |
| soybeans | 4 | 4 | 0 | 0 | 0 | 2 |
| wheat | 8/4 | 9 | 1 | 3 | 2 | 5/3 |
| corn | 2 | 3 | 0 | 1 | 1 | 2 |
| rice | 3 | 4 | 1 | 3 | 3 | 3 |

Since a relatively small amount of one or more of the active morpholinobenzimidazoles should be uniformly distributed over the area to be treated, the compounds preferably are formulated with conventional herbicide carriers, either liquid or solid. Thus, the compounds can be impregnated on or admixed with a pulverulent solid carrier such as lime, talc, clay, Bentonite, calcium chloride, vermiculite, and the like. Alternatively, the compounds can be dissolved or suspended in a liquid carrier such as water, kerosene, alcohols, diesel oil, mineral oil, xylene, benzene, glycols, ketones, and the like. Since many of the compounds will form water-soluble salts such as with mineral acids, they can be formulated with water.

A surfactant is preferably included to aid in dispersion, emulsification and coverage. The surfactant can be ionic or non-ionic and may be liquid or a solid. The use of the term "surfactant" herein is intended to include such compounds commonly referred to as wetting agents, dispersing agents and emulsifying agents. Typical surfactants include the alkylarylsulfonates, the fatty alcohol sulfates, sodium salt of naphthalenesulfonic acid, alkylaryl polyether alcohols, long chain quaternary ammonium compounds, sodium salts of petroleum-derived alkyl-sulfonic acids, polyoxyethylene-sorbitan monolaurate, and the like. These dispersing and wetting agents are sold under numerous trademarks and may either be pure compounds, mixtures of compounds of the same general group, or they can be mixtures of compounds of different classes. Surfactants can also be included in compositions containing a solid inert carrier.

Concentrated compositions containing the active agent which can be subsequently diluted, as with water, to the desired concentration for application to plants and soil are also provided. The advantages of such concentrates are that they are prepared by the manufacturer in a form such that the user need only mix them with a locally available carrier, preferably water, thereby keeping shipping costs to a minimum while providing a product which can be used with a minimum of equipment and effort. Such concentrates may contain from about 5 to about 95 percent by weight of one or more of the active morpholinobenzimidazoles with a carrier or diluent, which may be a liquid or a solid. Liquid carriers which are miscible with the active agent or other liquids in which the compound may be suspended or dispersed, can be used. A surfactant is also generally included to facilitate such dilution or dispersion in water. However, the surfactant itself may comprise the carrier in such concentrates.

The herbicidal compositions can include other beneficial adjuvants, such as humectants, oils and contact agents. Further, other herbicides such as the chlorophenoxyacetic acids, substituted uracils and ureas, triazines, thiocarbamates, carbamates, anilides, amides, and haloalkanoic acids, can be included in the formulation, if desired.

The following are representative examples of formulations containing the herbicidal compounds of this invention, in which the percent is by weight.

EXAMPLE 15

| Emulsifiable Concentrate | |
|---|---|
| 5-trifluoromethyl-1,2-(gamma-oxa-tetramethylene)benzimidazole | 13.3% |
| methyl isoamyl ketone | 61.3% |
| xylene | 20.4% |
| nonionic-anionic emulsifier (phosphate-type) | 5.0% |

EXAMPLE 16

| Wettable Powder | |
|---|---|
| 5-trifluoromethyl-1,2-(gamma-oxa-tetramethylene)benzimidazole | 53.2% |
| attaclay | 41.8% |
| lignin sulfonate dispersing agent | 4.0% |
| wetting agent (naphthalenesulfonate) | 1.0% |

The above components are blended, air-milled and then reblended. The powder is then dispersed in water for application to plants and soil.

Various changes and modifications of the invention can be made, and, to the extent that such variations incorporate the spirit of this invention, they are intended to be included within the scope of the appended claims.

What is claimed is:

1. The method for controlling weed growth which comprises applying to the locus of said weeds a phytotoxic amount of a compound of the formula

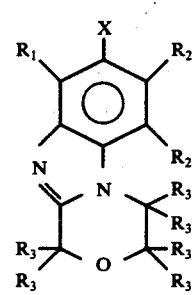

wherein X is selected from the group consisting of halo-lower alkyl, lower alkylsulfonyl, halo-lower alkylsulfonyl, halo and lower alkyl, $R_1$ represents hydrogen, lower alkyl or halo, each $R_2$ is selected from hydrogen, halo, lower alkyl, lower alkoxy, cyano, amino and nitro, and each $R_3$ is selected from hydrogen and lower alkyl.

2. The method in accordance with claim 1 in which said X is selected from trifluoromethyl, lower alkylsulfonyl, halo-lower alkylsulfonyl, and branched-chain alkyl of 3 to about 6 carbon atoms, $R_1$ represents hydrogen, chloro or $C_1$-$C_3$ alkyl, each $R_2$ is selected from hydrogen, chloro, $C_1$-$C_3$ alkyl, amino and nitro, and each $R_3$ is selected from hydrogen and $C_1$-$C_3$ alkyl.

3. The method in accordance with claim 1 in which said compound is applied at a rate of about 0.2 to 15 pounds per acre.

4. The method in accordance with claim 1 in which said compound is applied as a pre-emergence treatment to soil.

5. The method in accordance with claim 4 in which said compound is applied at a rate of about 0.5 to 5 pounds per acre.

6. The method in accordance with claim 5 in which said compound is incorporated in the upper layer of said soil.

7. The method in accordance with claim 1 in which said compound is applied as a post-emergence treatment at a rate of about 0.5 to 4 pounds per acre.

8. The method in accordance with claim 1 in which said compound is 5-methylsulfonyl-1,2-(gamma-oxa-tetramethylene)benzimidazole.

9. The method in accordance with claim 1 in which said compound is 5-trifluoromethyl-1,2-(gamma-oxa-tetramethylene)benzimidazole.

10. A compound of the formula

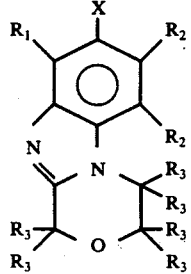

in which X is selected from the group consisting of trifluoromethyl, lower alkylsulfonyl, halo-lower alkylsulfonyl and branched chain alkyl of 3 to about 6 carbon atoms, $R_1$ is hydrogen, lower alkyl or halo, each $R_2$ is selected from hydrogen, halo, lower alkyl, lower alkoxy, cyano, amino and nitro and each $R_3$ is selected from hydrogen and lower alkyl.

11. A compound in accordance with claim 10 in which $R_1$ represents hydrogen, chloro, or $C_1$-$C_3$ alkyl, each $R_2$ is selected from hydrogen, chloro, $C_1$-$C_3$ alkyl, amino and nitro and each $R_3$ is selected from hydrogen and $C_1$-$C_3$ alkyl.

12. The compound according to claim 10, 5-trifluoromethyl-1,2-(gamma-oxa-tetramethylene)benzimidazole.

13. The compound according to claim 10, 5-methylsulfonyl-1,2-(gamma-oxa-tetramethylene)benzimidazole.

14. The compound according to claim 10, 5-isopropyl-1,2-(gamma-oxa-tetramethylene)benzimidazole.

15. The compound according to claim 10, 5-tert-butyl-1,2-(gamma-oxa-tetramethylene)benzimidazole.

16. A herbicidal composition comprising a compound of the formula of claim 10, a surfactant and a carrier therefor.

17. The method in accordance with claim 1 in which said compound is 5-isopropyl-1,2-(gamma-oxa-tetramethylene)benzimidazole.

18. The method in accordance with claim 1 in which said compound is 5-tert-butyl-1,2-(gamma-oxa-tetramethylene)benzimidazole.

* * * * *

UNITED STATES PATENT OFFICE
CERTIFICATE OF CORRECTION

Patent No. 4,049,422                    Dated September 20, 1977

Inventor(s) Kelvin Kei-Wei Shen & Wayne Stuart Belles

It is certified that error appears in the above-identified patent and that said Letters Patent are hereby corrected as shown below:

| Column | Line | Change |
|---|---|---|
| 3 | 42 | Delete "formica" and add -- formic -- |
| 4 | 2 | Delete "6-Amino-5trifluoromethyl-" and Add -- 6-Amino-5-trifluoromethyl- -- |
| 8 | 45 | Delete "cyano-OB" and Add -- cyano-OTB -- |
| 10 | 34 | In the line between "rice" and "lambsquarters" insert the following headings: |

-- Plants      Compound G      Compound H      Compound J 1 lb.  2 lb.   1 lb.  2 lb.    1 lb.  2 lb.   ---

Signed and Sealed this

Seventeenth Day of January 1978

[SEAL]

Attest:

RUTH C. MASON
Attesting Officer

LUTRELLE F. PARKER
Acting Commissioner of Patents and Trademarks